United States Patent
Rilhac et al.

(10) Patent No.: US 11,957,781 B2
(45) Date of Patent: Apr. 16, 2024

(54) *SWERTIA CHIRATA* EXTRACT AND COSMETIC COMPOSITIONS COMPRISING SAME

(71) Applicant: CHANEL PARFUMS BEAUTE, Neuilly sur Seine (FR)

(72) Inventors: Vincent Rilhac, Pantin (FR); Maeva Gillet, Pantin (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 1 day.

(21) Appl. No.: 17/692,858

(22) Filed: Mar. 11, 2022

(65) Prior Publication Data
US 2022/0296497 A1 Sep. 22, 2022

(30) Foreign Application Priority Data

Mar. 22, 2021 (EP) ..................................... 21305353

(51) Int. Cl.
- *A61K 36/00* (2006.01)
- *A61K 8/73* (2006.01)
- *A61K 8/9789* (2017.01)
- *A61Q 19/00* (2006.01)
- *A61Q 19/08* (2006.01)

(52) U.S. Cl.
CPC ............ *A61K 8/9789* (2017.08); *A61K 8/731* (2013.01); *A61Q 19/007* (2013.01); *A61Q 19/08* (2013.01); *A61K 2800/74* (2013.01); *A61K 2800/805* (2013.01)

(58) Field of Classification Search
CPC ..................................................... A61K 36/51
See application file for complete search history.

(56) References Cited

U.S. PATENT DOCUMENTS

2017/0020796 A1 1/2017 Bezivin

FOREIGN PATENT DOCUMENTS

| CN | 102302586 A | | 1/2012 |
|---|---|---|---|
| CN | 103877051 A | | 6/2014 |
| CN | 10438819 A | * | 3/2015 |
| EP | 1928447 B1 | | 2/2016 |
| JP | 2011148783 A | | 8/2011 |

OTHER PUBLICATIONS

European Search Report dated Oct. 19, 2021, in corresponding to European Application No. 21305353.1; 7 pages.

Gnpd Mintel: "Restorative Cream Product Details Company Indeed Laboratories, Canada Brand Indeed Laboratories Me-NO-Pause Category SkincareFace/Neck Care Market UK Imported Product Company & Source Details Store Name FeelUnique Store Type Internet/Mail Order Product Description"; Nov. 1, 2020; XP055850054; 3 pages.

Kaur Prabhjot et al., "Simultaneous quantification of aleanolic acid, ursolic acid, betulinic acid and lupeol in different populations of fiveSwertiaspecies by using HPTLC-densitometry: Comparison of different extraction methods and solvent selection"; Industrial Crops and Products 2019; Elsevier; vol. 130; XP085588838; pp. 537-546.

Vijay Kumar et al., "A Review of *Swertia chrirayita* (Gentianaceae) as a Traditional Medicinal Plant"; Frontiers in Pharmacology; Jan. 12, 2016; vol. 6; Article 308; XP055467762; pp. 1-14.

Hanif, et al. "Antibacterial and Antifungal Activities of Essential Oils Extracted from Medicinal Plants Using CO2 Supercritical Fluid Extraction Technology." Asian Journal of Chemistry, Nov. 2010, vol. 22, No. 10, https://www.researchgate.net/publication/286878398, pp. 7787-7798.

* cited by examiner

*Primary Examiner* — Qiuwen Mi
(74) *Attorney, Agent, or Firm* — Maier & Maier, PLLC

(57) ABSTRACT

A *Swertia chirata* extract obtained by extracting with supercritical $CO_2$ an alcoholic extract of *Swertia chirata*, and to a cosmetic composition including such an extract having in particular an anti-ageing effect for the skin. Also, administering such an extract in a cosmetic method for preventing and/or reducing skin ageing and a cosmetic method for hydrating the skin and/or improving the barrier function of the skin.

20 Claims, 2 Drawing Sheets

SWERTIA CHIRATA EXTRACT AND COSMETIC COMPOSITIONS COMPRISING SAME

Chanel Parfums Beauté wishes to thank the National Biodiversity Centre of Bhutan for its assistance in setting up the supply channel and the culturing of the *Swertia chirata* plant and also in the application of the Nagoya protocol.

We sincerely thank the general secretary Mr Dasho Rinzin Dorji, the programme director Dr Tashi Yangzome Dorji and the entire Bioprospecting team: Mr Chencho Dorji, Mr Mani Prasad Nirola, Mrs Jamyang Choden and quite particularly Mr Leki Wangchuk, for their support and advice.

FIELD

The present invention relates to a *Swertia chirata* extract, the method for obtaining same, a cosmetic composition comprising same, and also various cosmetic uses.

BACKGROUND

The skin consists mainly of three layers, namely, starting from the most superficial, the epidermis, the dermis and the hypodermis.

The outer layer of the skin, the epidermis, consists of keratinocytes (in the majority), melanocytes (involved in skin pigmentation) and Langerhans cells. Its function is to protect the body against the outside environment and to ensure its integrity, and in particular to slow down the penetration of microorganisms or of chemical substances, and to prevent evaporation of the water contained in the skin.

To do this the keratinocytes undergo a continuous oriented maturation process during which the keratinocytes located in the basal layer of the epidermis form, at the terminal stage of their differentiation, corneocytes which are totally keratinized dead cells in the form of cornified envelopes consisting of proteins and lipids such as ceramides. During this differentiation process, intercorneocyte epidermal lipids are also formed and then organized in the form of bilayers (sheets) in the stratum corneum. They participate, with the abovementioned cornified envelopes, in the barrier function of the epidermis.

As the skin ages, it becomes thinner, loses volume and elasticity and its barrier function is impaired. The dermoepidermal junction is one of the preferred targets of skin ageing. Its main function is to allow cohesion between the epidermis and the dermis in order to ensure the functions of cohesion and nutrition of the skin. These functions are based mainly on the action of the extracellular matrix which is produced by the keratinocytes. This matrix consists of an assembly of several macromolecules, including collagen, proteoglycans, glycosaminoglycans (including hyaluronic acid), elastin and structural glycoproteins. Cellular ageing and the action of environmental factors such as UV radiation or pollution will detrimentally modify these extracellular matrix components. They will undergo enzymatic degradation, in particular by the action of matrix metalloproteinases (MMPs); the matrix will no longer be able to correctly perform its functions, which will cause fragilities and a decrease in cell regeneration capacity and will be responsible for the appearance of wrinkles and fine lines on the skin.

The extracellular matrix and the prevention of the degradation thereof, resulting in particular from the action of enzymes such as MMPs, have become preferred targets in the prevention and reduction of skin ageing.

As a result, there is a real need to provide active agents capable of acting on the maintenance of the extracellular matrix functions and in particular on the prevention of the degradation of the extracellular matrix in order to combat the detrimental modifications caused by skin ageing.

Furthermore, because of an ever increasing desire by consumers for natural products containing as few synthetic ingredients as possible, and the increasingly extensive regulatory constraints affecting compounds derived from the chemical industry, it would be advantageous for such active agents to be derived from plant extracts.

It is also necessary to search for extraction methods that are more environmentally friendly, using recyclable and non-toxic solvents while at the same time allowing selective extraction of the molecules of interest without degrading them.

SUMMARY

*Swertia chirata* is a plant of the *Swertia* genus, a genus which belongs to the family Gentianaceae and which contains approximately 150 species. *Swertia chirata* is in particular used in traditional medicine in India, in Bhutan and in Nepal, from where it originates. Its roots, which are reputed to be the most bioactive part of the plant, are used to treat various conditions such as fever, malaria, asthma, certain liver pathologies, diabetes or else certain types of mental disorders.

Entirely surprisingly, the authors of the present invention have succeeded in demonstrating that it is possible to obtain *Swertia chirata* extracts which have noteworthy anti-ageing and barrier-function-protecting properties by subjecting an alcoholic extract of *Swertia chirata* to a step of extraction with supercritical $CO_2$. The inventors have in particular demonstrated that these extracts make it possible, on the one hand, to inhibit the process of inflammation and degradation of the extracellular matrix mediated by epidermal keratinocytes, and on the other hand, to stimulate the lipid metabolism of keratinocytes and to stimulate the synthesis of extracellular matrix components. These extracts can therefore be used for preventing/slowing down skin ageing resulting from the disorganization and the degradation of the extracellular matrix, but also for improving the barrier function and the hydration of the skin.

The *Swertia chirata* extracts according to the invention are in addition advantageously compatible with all the pharmaceutical presentation forms: not only can they be used in cosmetic compositions such as creams, or gel creams, but they can also be advantageously introduced into compositions comprising only an aqueous phase, such as lotions, or into compositions comprising only a non-aqueous phase, for example in the form of oils.

Thus, according to a first aspect, the present invention relates to a method for preparing a *Swertia chirata* extract, comprising a step of extracting, with supercritical $CO_2$, an alcoholic extract of *Swertia chirata*, at a temperature of between 40 and 80° C., preferably between 50 and 70° C. and at a pressure of between 20 and 60 MPa, preferably between 25 and 35 MPa.

A subject of the invention is also a *Swertia chirata* extract obtained by such a method, and also a cosmetic composition comprising, in a physiologically acceptable medium, such a *Swertia chirata* extract.

Finally, a subject of the invention is also the non-therapeutic, cosmetic use of a *Swertia chirata* extract as described above, for preventing and/or reducing skin ageing, but also for hydrating the skin and/or improving the barrier function of the skin.

DETAILED DESCRIPTION

*Swertia chirata*

Figure 1:
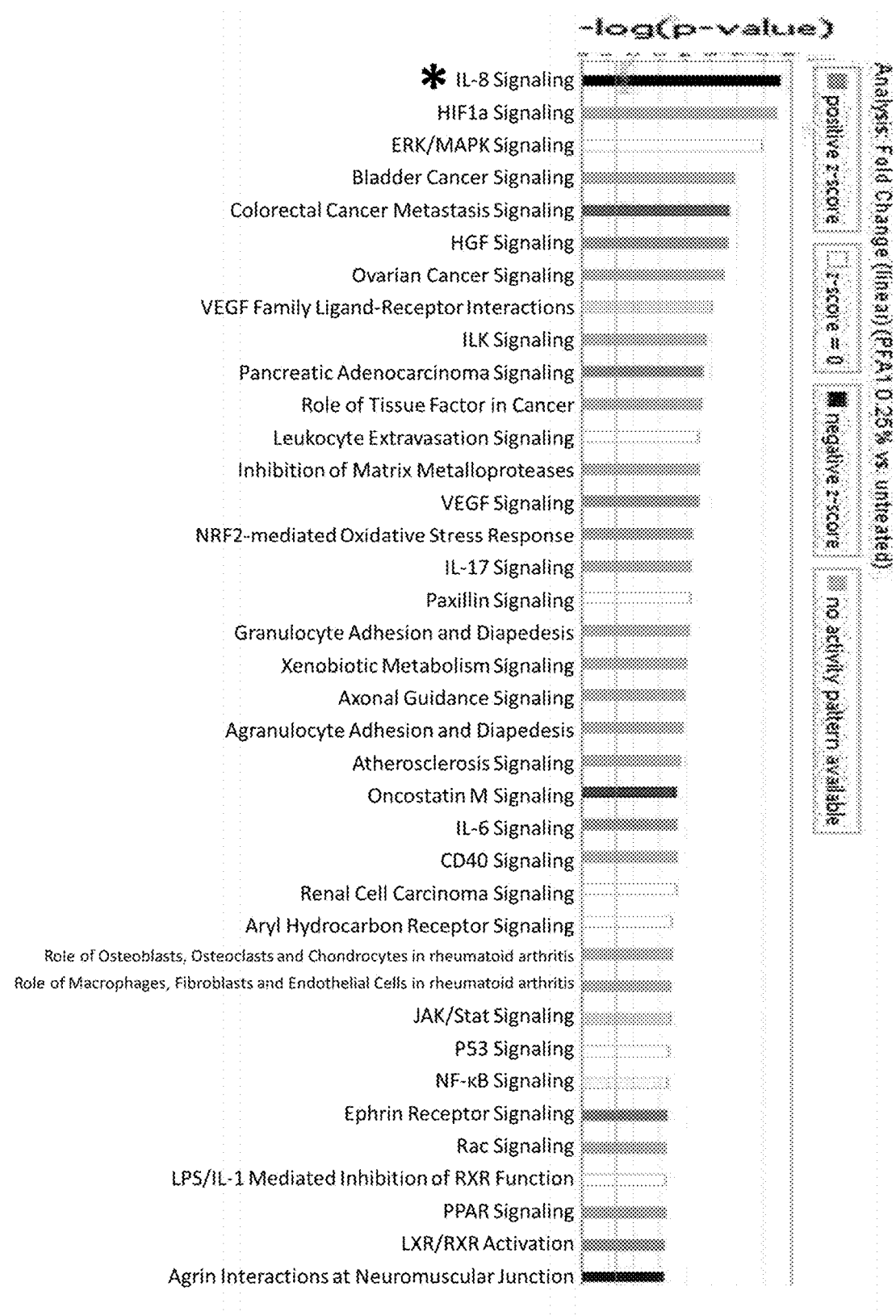
FIG. 1 is a graph representing the biological pathways modulated by the *Swertia chirata* extract C1 at 0.25% in normal human epidermal keratinocytes after 48 h of treatment.

*Swertia chirata*, also called *Swertia chirayta*, *Swertia chirayita* or else chiretta is a herbaceous plant belonging to the family Gentianaceae and to the genus *Swertia*. It is found on the Himalayan plateaux, in particular in India, in Nepal and in Bhutan. It is an erect annual/biannual herbaceous plant 60 to 150 cm high, which has a stem that is cylindrical from its base to its middle, and quadrangular on its upper part. Its stem is orangey-brown, or even purplish-blue, with a yellow core. Its leaves are lanceolate, opposite, sessile, acuminate and are approximately 4 to 10 cm long. It has numerous flowers, which are tetrameric and a violet-tinted yellowish-green colour.

The *Swertia chirata* extract according to the invention is obtained from the whole plant, that is to say from the parts comprising the flowers, the leaves, the stem and the roots of the plant.

Method for Preparing a *Swertia chirata* Extract

The method for preparing a *Swertia chirata* extract according to the present invention comprises a step of extracting, with supercritical $CO_2$, an alcoholic extract of *Swertia chirata*, at a temperature of between 40 and 80° C., preferably between 50 and 70° C. and at a pressure of between 20 and 60 MPa, preferably between 25 and 35 MPa.

The applicant has in fact demonstrated that by performing a second extraction of an alcoholic extract of *Swertia chirata* by means of supercritical $CO_2$, it is possible to obtain extracts having noteworthy anti-ageing and barrier-function-stimulating properties.

The extraction with supercritical $CO_2$ is carried out at a temperature of between 40 and 80° C., preferably between 50 and 70° C., for example at 60° C., and at a pressure of between 20 and 60 MPa, preferably between 25 and 35 MPa, for example 30 MPa.

In the context of the present invention, it should be noted that a value range of between "A" and "B", like the temperature above which is between 40 and 80° C., comprises all the values between A and B, limits included. The step of extracting with supercritical $CO_2$ according to the present invention can therefore be carried out at any temperature value between 40 and 80° C., but also at 40 or 80° C. This applies for all the value ranges disclosed in the context of the present invention.

According to one preferred embodiment, the $CO_2$ flow rate is at least 150 g/min, preferably 200 g/min.

The extraction with supercritical $CO_2$ is preferentially carried out in the presence of an alcoholic solvent. The alcoholic solvent may be a monoalcohol comprising from 2 to 4 carbon atoms, preferentially ethanol. According to one preferred embodiment, the extraction with supercritical $CO_2$ is carried out in the presence of ethanol, preferentially ethanol at 60°.

According to one particular embodiment, the alcoholic solvent, preferably ethanol, is introduced in a content of between 1 and 10% relative to the total weight of the mixture comprising the supercritical $CO_2$ and the alcoholic solvent.

The extraction with supercritical $CO_2$ has the advantage of requiring only a small consumption of solvents (the supercritical $CO_2$, which is the major solvent, is recycled), of using non-toxic solvents and of being an environmentally friendly method.

The extraction solvents (mixture comprising the supercritical $CO_2$ and optionally the alcoholic solvent) are used in the step of extracting with supercritical $CO_2$ in a weight ratio of the extraction solvents relative to the alcoholic extract of between 40 and 150, preferentially 75.

In the context of the present invention, the "alcoholic extract" which undergoes the step of extracting with supercritical $CO_2$ is an extract which has been obtained by means of a step of extracting *Swertia chirata* with at least one alcoholic solvent, and which has therefore undergone a step of "alcoholic extraction". The alcoholic solvent is as defined above. It may be the same or another alcoholic solvent with respect to the one used for the step of extracting with supercritical $CO_2$. According to one preferred embodiment, the alcoholic solvent used for the alcoholic extraction step is ethanol, more preferentially ethanol at 60°.

All the parts of *Swertia chirata* can be extracted with the alcoholic solvent in "fresh" form, that is to say within 48 hours, particularly 24 hours, even more particularly 12 hours, following harvesting.

All the parts of *Swertia chirata* can also be extracted in dry form. In this case, the fresh plant is dehydrated under mild conditions, either at ambient temperature in the dark or in a ventilated dryer at a temperature of less than 35° C. The plant is preferably dried until a solids content greater than 80% and preferentially greater than 85% is obtained.

All the parts of *Swertia chirata* can also be milled in order to obtain a powder comprising particles having a size of less than 5 cm, preferably less than 2 cm.

All the parts of *Swertia chirata*, in fresh form or in dry form, whole or milled, are subjected to at least one step of extraction with at least one alcoholic solvent (alcoholic extraction step) in order to obtain the alcoholic extract of *Swertia chirata* used in the context of the present invention. The plant/alcoholic solvent ratio for this alcoholic extraction step is typically 1 to 10 (weight/weight), and this step lasts at least 1 hour, preferably at least 2 hours, in particular at least 3 hours, and can be repeated once or twice. The alcoholic extract obtained at the end of this alcoholic extraction step is filtered, for example by sieving, in order to remove the plant residues. The alcoholic extract can, for example, be filtered at 100 μm, particularly 10 μm, preferentially 1 μm.

The alcoholic extract can also be decolorized, for example after the filtration step. This step is aimed at removing the pigments present in the extract (predominantly chlorophyll). Those skilled in the art are aware of several methods for removing the pigments present in plant extracts. The decolorizing can, for example, be carried out by bringing the extract into contact with active carbon. Once the decolorizing has been carried out, the mixture is filtered in order to remove the carbon residues.

It is therefore this alcoholic extract of *Swertia chirata*, obtained after at least one step of alcoholic extraction of

*Swertia chirata*, and optionally a filtration and/or decolorizing step, which will be subjected to the extraction with supercritical $CO_2$.

In one particular embodiment, the alcoholic extract is combined with a support such as a polysaccharide, for instance starch, maltodextrin, or preferably cellulose, before being subject to the extraction with supercritical $CO_2$. In this context, the polysaccharide is added to the alcoholic extract: the alcoholic extract content ranges from 50 to 70% by weight relative to the total weight of the mixture comprising the alcoholic extract and the polysaccharide, and the polysaccharide (preferably cellulose) content ranges from 30 to 50% by weight, relative to the total weight of the mixture comprising the alcoholic extract and the polysaccharide.

According to this particular embodiment, the alcoholic solvent, preferentially ethanol, present in the alcoholic extract+polysaccharide mixture can be removed, typically by evaporation, for example by evaporation under vacuum, in order to obtain only a mixture of polysaccharide/dry extract, that is to say comprising 100% by weight of solids. This mixture can then be milled in order to obtain a polysaccharide/dry extract powder comprising particles having a size of less than 2 cm, preferably less than 1 cm. According to this embodiment, it is this powder which is subjected to the step of extracting with supercritical $CO_2$ in the context of the method of the present invention.

Thus, according to one particular embodiment, the method for preparing a *Swertia chirata* extract according to the present invention comprises the following steps:
- a) extracting *Swertia chirata*, preferably in powder form, with at least one alcoholic solvent, preferably ethanol;
- b) filtering the mixture obtained in a) in order to remove the plant residues;
- b') optionally, decolorizing the mixture obtained at the end of step b);
- c) adding a polysaccharide, preferably cellulose, to the mixture thus obtained in order to obtain a polysaccharide/dry extract mixture in the alcoholic solvent;
- d) removing the alcoholic solvent, preferably by evaporation;
- e) milling the dry extract/polysaccharide mixture obtained at the end of step d) in order to obtain a powder; and
- f) extracting with supercritical $CO_2$ the powder obtained at the end of step e) at a temperature between 40 and 80° C., preferably between 50 and 70° C. and at a pressure of between 20 and 60 MPa, preferably between 25 and 35 MPa.

The *Swertia chirata* extract obtained at the end of the step of extracting with supercritical $CO_2$ is the extract according to the invention.

This extract can also be treated and finalized for cosmetic purposes, so that it can be integrated into a cosmetic composition. This treatment is carried out by conventional means, known to those skilled in the art, for example via steps of dilution, of combination with a cosmetic support, of evaporation of the solvents or else of filtration.

In this context, the extract contained in the solvent used for the extraction with supercritical $CO_2$ (that is to say the liquid phase obtained at the end of the step of extracting with supercritical $CO_2$) can undergo a filtration step, for example to 1 µm.

The extract can then be diluted in an oil such as plant oils or esterified oils, for instance caprylic/capric triglyceride or preferably 2-ethylhexyl palmitate, for example at 1%.

The alcoholic solvent can be removed before or after dilution in the oil, for example by evaporation, preferably by evaporation under vacuum.

The extract diluted in the oil can then be filtered again, for example to 1 µm in order to remove the insoluble substances and thus to obtain the final extract.

According to this embodiment, the method above can therefore also comprise the following steps g) to i):
- g) filtering the extract contained in the solvent used for the extraction with supercritical $CO_2$, and optionally removing the alcoholic solvent, preferably by evaporation;
- h) diluting the extract obtained at the end of step g) in an oil, preferably 2-ethylhexyl palmitate, and optionally removing the residual alcoholic solvent, preferably by evaporation;
- i) filtering the diluted extract obtained at the end of step h).

According to this embodiment, the method for preparing a *Swertia chirata* extract according to the present invention can therefore comprise the following steps:
- a) all the parts of *Swertia chirata* previously dried and milled to a fineness of less than 2 cm are extracted twice by maceration in ethanol at 60° C. for 2 h with a solvent/plant ratio of 10/1;
- b) the extract thereby obtained is subsequently sieved at 100 µm and then filtered to 1 µm in order to remove the plant residues;
- b') the extract is decolorized with 30% active carbon relative to the dry extract and subsequently filtered again at 1 µm in order to remove the residual carbon;
- c) cellulose is added to the extract in order to obtain a cellulose (40%)/dry extract (60%) mixture in ethanol;
- d) the ethanol is subsequently evaporated off in order to obtain only the cellulose/dry extract mixture;
- e) the cellulose/dry extract mixture is subsequently milled to a fineness of less than 1 cm in order to obtain a powder;
- f) the powder obtained is subsequently extracted with a supercritical $CO_2$ (95%)/ethanol (5%) mixture at 60° C., at 500 bar (50 MPa) and with a flow rate of 200 g/min until the weight ratio of the supercritical $CO_2$ (95%)/ethanol (5%) mixture relative to the alcoholic extract is 75;
- g) the obtained extract contained in the ethanol is filtered at 1 µm;
- h) the extract obtained at the end of step g) is diluted to 1% in 2-ethylhexyl palmitate and the ethanol is evaporated off;
- i) the extract is subsequently filtered at 1 µm in order to remove the insoluble substances and to obtain the final extract (referred to herein as "extract C1").

According to an alternative embodiment, the residual powder, which contains the polysaccharide such as cellulose and a part of the *Swertia chirata* extract, obtained at the end of the step of extracting the supercritical $CO_2$ (that is to say the solid phase obtained at the end of the step of extracting with supercritical $CO_2$) can be suspended in an alcoholic solvent, preferably ethanol. The alcoholic solvent is defined as above and can be the same or another alcoholic solvent with respect to the one used for the alcoholic extraction step and/or for the step of extracting with supercritical $CO_2$.

The mixture containing the residual powder in suspension in the alcoholic solvent can subsequently be filtered, for example to 1 µm, in order to remove the cellulose.

The extract can subsequently be diluted in a glycol such a caprylyl glycol, pentylene glycol, or preferably propanediol, for example to 1%.

The alcoholic solvent can be removed before or after dilution in the glycol, for example by evaporation, preferably by evaporation under vacuum.

The extract diluted in the glycol can then be filtered again, for example to 1 µm, in order to remove the insoluble substances and to thus obtain the final extract.

According to this alternative embodiment, the method comprising steps a) to f) above can therefore also comprise the following steps g1) to j1):

- g1) dissolving the residual powder obtained at the end of step f) in an alcoholic solvent, preferably ethanol;
- h1) filtering the mixture obtained at the end of step g1) and optionally removing the alcoholic solvent, preferably by evaporation;
- i1) diluting the extract obtained at the end of step h1) in a glycol, preferably propanediol, and optionally removing the residual alcoholic solvent, preferably by evaporation;
- j1) filtering the diluted extract obtained at the end of step i1).

According to this alternative embodiment, the method for preparing a *Swertia chirata* extract according to the present invention can therefore comprise the following steps:

- a) all the parts of *Swertia chirata* previously dried and milled to a fineness of less than 2 cm are extracted twice by maceration in ethanol at 60° C. for 2 h with a solvent/plant ratio of 10/1;
- b) the extract obtained is subsequently sieved at 100 µm and then filtered to 1 µm in order to remove the plant residues;
- b') the extract is decolorized with 30% active carbon relative to the dry extract and subsequently filtered again at 1 µm in order to remove the residual carbon;
- c) cellulose is added to the extract in order to obtain a cellulose (40%)/dry extract (60%) mixture in ethanol;
- d) the ethanol is subsequently evaporated off in order to obtain only the cellulose/dry extract mixture;
- e) the cellulose/dry extract mixture is then milled to a fineness of less than 1 cm in order to obtain a powder;
- f) the powder obtained is subsequently extracted with a supercritical $CO_2$ (95%)/ethanol (5%) mixture at 60° C., at 500 bar (50 MPa) and with a flow rate of 200 g/min until the weight ratio of the supercritical $CO_2$ (95%)/ethanol (5%) mixture relative to the alcoholic extract is 75;
- g1) the residual powder present at the end of step f) is then recovered and put back into solution in ethanol with stirring at 45° C.;
- h1) the mixture is then filtered at 1 µm in order to remove the cellulose;
- i1) the extract is then diluted to 1% in propanediol and the ethanol is evaporated off under vacuum;
- j1) the extract is subsequently filtered at 1 µm in order to remove the insoluble substances and to obtain the final extract (referred to herein as "extract C2").

Swertia chirata Extract

The invention that is the subject of the present application also covers a *Swertia chirata* extract obtained by the method described above.

Cosmetic Composition

A subject of the present invention is also a cosmetic composition comprising, in a physiologically acceptable medium, at least one *Swertia chirata* extract obtained according to the method of the present invention.

The composition used according to the invention generally comprises, in addition to the extract described above, a physiologically acceptable and preferably cosmetically acceptable medium, that is to say one which is suitable for use in contact with human skin without any risk of toxicity, incompatibility, instability or allergic response, and in particular which does not cause feelings of discomfort (redness, tautness, stinging).

Advantageously, said cosmetic or dermatological composition can be in the form of a powder, an emulsion, a microemulsion, a nanoemulsion, a suspension, a solution, a lotion, a cream, an aqueous or aqueous-alcoholic gel, a foam, a serum, a solution or a dispersion for an aerosol, or a dispersion of lipid vesicles.

In the case of an emulsion, it may be a water-in-oil or oil-in-water emulsion.

The cosmetic or dermatological composition according to the invention may also comprise a solvent chosen as a function of the various ingredients and of the administration form.

By way of examples, mention may be made of water (preferably demineralized water or floral waters), or an alcohol such as ethanol.

Said cosmetic composition may also comprise, in addition to the extract according to the invention, at least one usual additive in the field, such as for example at least one compound chosen from an emollient or humectant, a gelling agent and/or thickener, a surfactant, an oil, an active agent, a dye, a preservative, an antioxidant, an organic or inorganic powder, a sunscreen and a fragrance:

One or more humectant(s), such as polyols (glycerol, diglycerol, propanediol, caprylyl glycol, pentylene glycol, hexanediol), sugars, glycosaminoglycans such as hyaluronic acid and salts and esters thereof; and polyquaterniums such as Lipidure PMB.

Said humectant will be present in the composition at a content of about from 0.1 to 30%, preferably 0.005 to 10% by total weight of the composition.

One or more emollient(s) which can be chosen for example from esters such as jojoba esters, fatty acid esters of a fatty alcohol (octyldodecyl myristate, triethylhexanoin, dicaprylyl carbonate, isostearyl isostearate, caprylic/capric triglyceride), butters such as shea butters (*Butyrospermum parkii* butter extract, shea butter ethyl esters, sold under the names Lipex Sheasoft, Lipex Shea-U, Lipex Shea, Lipex Shealight, Lipex Shea Tris) or moringa butters (moringa oil/hydrogenated moringa oil esters), waxes (*Acacia decurrens* flower wax & *Helianthus annuus* seed cera (seed wax), C10-18 triglycerides), plant oils, phytosqualane, alkanes (undecane, tridecane).

Said emollient will be present in the composition at a content of about from 0.1 to 30%, preferably 0.5 to 10% by total weight of the composition.

One or more aqueous-phase-gelling agent(s) and/or aqueous-phase-thickener(s), chosen for example from cellulose-based derivatives, gums of plant origin (guar, locust bean, alginates, carrageenans, pectins), or of microbial origin (xanthan), clays (laponite), hydrophilic or amphiphilic, crosslinked or non-crosslinked homopolymers and copolymers of acryloylmethylpropanesulfonic acid (AMPS) and/or of acrylamide and/or of acrylic acid and/or of acrylic acid salts or esters (sold under the names Aristoflex AVC, Aristoflex AVS, Aristoflex HMB, Simulgel NS, Simulgel EG, Simulgel 600, Simulgel 800, Pemulen, Carbopol, Sepiplus 400, Seppimax Zen, Sepiplus S, Cosmedia SP).

Said gelling agent and/or thickener will be present in the composition at a content of about from 0.1 to 10% by total weight of the composition.

One or more surfactant(s), such as lecithins, polyglycerol derivatives, sugar derivatives (derivatives of glucosides or of xylosides sold under the name Montanov 68, Montanov 202, Montanov 82, Montanov L, Easynov), phosphates (C20-22 alkyl phosphate sold under the name Sensanov WR).

Said surfactant will be present in a content of about 0.1 to 8%, preferably 0.5 to 3% by weight, relative to the total weight of the composition.

One or more active agent(s) of natural, biotechnological or synthetic origin having a biological activity and having an efficacy on the skin via biological sites, for example chosen from vitamins such as vitamin C and derivatives thereof (ascorbyl glucoside, 3-O-ethyl ascorbic acid, ascorbyl tetraisopalmitate), vitamin A and derivatives thereof, vitamin E and derivatives thereof, vitamin B3 or niacinamide, panthenol, trace elements, allantoin, adenosine, peptides (palmitoyl tetrapeptide-7, palmitoyl tripeptide-1, palmitoyl pentapeptide-4, acetyl dipeptide-1 cetyl ester, acetyl tetrapeptide-5, sold under the name NP Rigin, Matrixyl 3000, Idealift, Eyeseryl), plant extracts (*Glycyrrhiza glabra* extract, *Centella asiatica* leaf extract, *Secale cereale* seed extract), yeast extracts, alpha-hydroxy acids such as glycolic or lactic acid, tranexamic acid and derivatives thereof such as cetyl tranexamic ester, etc.

Said active agent will be present in the composition at a content of about from 0.1 to 10% by total weight of the composition.

Other additives customarily used in cosmetics may also be present in the composition according to the invention, in particular preservatives, antioxidants or fragrances well known in the technical field.

Those skilled in the art are in a position to choose, from all of these optional additives, both the nature and the amount of those that will be added to the composition, in such a way that said composition retains all of its properties.

Non-Therapeutic, Cosmetic Use of the *Swertia Chirata* Extract According to the Invention A subject of the invention is also the non-therapeutic, cosmetic use of a *Swertia chirata* extract according to the invention, for preventing and/or reducing skin ageing.

In this embodiment, the extract or the composition is applied to detrimentally modified but non-pathological skin.

A subject of the invention is also the non-therapeutic, cosmetic use of a *Swertia chirata* extract according to the invention, for hydrating the skin and/or improving the barrier function of the skin, as a hydrating and/or soothing agent.

A subject of the invention is in addition the non-therapeutic, cosmetic use of a *Swertia chirata* extract according to the invention as an agent which inhibits the activity of matrix metalloproteinases (MMPs).

Finally, a subject of the invention is also the non-therapeutic, cosmetic use of a *Swertia chirata* extract according to the invention as an agent which stimulates the expression of genes encoding the constituent elements of the extracellular matrix, in particular stimulating the expression of genes encoding laminins and proteoglycans.

The invention will now illustrated by the following non-limiting examples.

EXAMPLES

Example 1: Preparation and Characterization of the *Swertia chirata* Extracts

>Extract 1 (extract "C1" or "PFAC1") is obtained by means of the following preparation method:

a) all the parts of *Swertia chirata* previously dried and milled to a fineness of less than 2 cm are extracted twice by maceration in ethanol at 60° C. for 2 h with a solvent/plant ratio of 10/1;

b) the extract obtained is subsequently sieved at 100 μm and then filtered to 1 μm in order to remove the plant residues;

b') the extract is decolorized with 30% of active carbon relative to the dry extract and subsequently filtered again at 1 μm in order to remove the residual carbon;

c) cellulose is added to the extract in order to obtain a cellulose (40%)/dry extract (60%) mixture in ethanol;

d) the ethanol is subsequently evaporated off in order to obtain only the cellulose/dry extract mixture;

e) the cellulose/dry extract mixture is subsequently milled to a fineness of less than 1 cm in order to obtain a powder;

f) the powder obtained is subsequently extracted with a supercritical $CO_2$ (95%)/ethanol (5%) mixture at 60° C. at 500 bar (50 MPa) and with a flow rate of 200 g/min until the powder can no longer be extracted;

g) the obtained extract contained in the ethanol is filtered at 1 μm;

h) the extract is diluted to 1% in 2-ethylhexyl palmitate and then left overnight at 4° C., and the ethanol is evaporated off;

i) the extract is subsequently filtered at 1 μm in order to remove the insoluble substances and to obtain the final extract.

After analysis, it was determined that extract 1 comprised 0.053% by weight of xanthones, including 0.015% of norswertianin, 0.006% of swertianin, 0.002% of bellidin and 0.03% of hydroxyxanthone derivatives. Extract 1 also comprises 0.03% by weight of oleanolic/ursolic acid (triterpenes). This extract does not comprise any detectable swertiamarin.

This extract is an oily extract enriched in non-polar molecules. It can therefore be advantageously integrated into oily/non-aqueous compositions.

>Extract 2 (extract "C2" or "PFAC2") is obtained by means of the following preparation method:

a) all the parts of *Swertia chirata* previously dried and milled to a fineness of less than 2 cm are extracted twice by maceration in ethanol at 60° C. for 2 h with a solvent/plant ratio of 10/1;

b) the extract obtained is subsequently sieved at 100 μm and then filtered to 1 μm in order to remove the plant residues;

b') the extract is decolorized with 30% of active carbon relative to the dry extract and subsequently filtered again at 1 μm in order to remove the residual carbon;

c) cellulose is added to the extract in order to obtain a cellulose (40%)/dry extract (60%) mixture in ethanol;

d) the ethanol is subsequently evaporated off in order to obtain only the cellulose/dry extract mixture;

e) the cellulose/dry extract mixture is subsequently milled to a fineness of less than 1 cm in order to obtain a powder;

f) the powder obtained is subsequently extracted with a supercritical $CO_2$ (95%)/ethanol (5%) mixture at 60° C. at 500 bar (50 MPa) and with a flow rate of 200 g/min until the powder can no longer be extracted;

g1) the residue present at the end of step f) is then recovered and put back into solution in ethanol with stirring at 45° C.;

h1) the mixture is filtered at 1 μm in order to remove the cellulose;

i1) the dry extract is then diluted to 1% in propanediol and the ethanol is evaporated off;

j1) the extract is subsequently filtered at 1 µm in order to remove the soluble substances and to obtain the final extract.

After analysis, it was determined that extract 2 comprised 0.134% by weight of xanthones, including 0.052% of mangiferin, 0.006% of norswertianin, 0.039% of 3-O-demethylswertipunicoside, 0.001% of bellidin, 0.019% of dixanthone and 0.002% of hydroxyxanthone derivatives. Extract 2 also comprises 0.035% of swertiamarin, 0.282% by weight of sugars/polyols, 0.038% by weight of oleanolic/ursolic acid (triterpenes), 0.024% of minerals and less than 0.001% of amarogentin.

This extract is an aqueous-alcoholic extract enriched in polar molecules. It can therefore be advantageously integrated into aqueous compositions.

>A comparative ethanolic extract (extract "EtOH") is obtained by means of the following preparation method:

a) all the parts of *Swertia chirata* previously dried and milled to a fineness of less than 2 cm are extracted twice by maceration in ethanol at 60° C. for 2 h with a solvent/plant ratio of 10/1;

b) the extract obtained is subsequently sieved at 100 µm and then filtered to 1 µm in order to remove the plant residues;

b') the extract is decolorized with 30% of active carbon relative to the dry extract and subsequently filtered again at 1 µm in order to remove the residual carbon;

i1) the extract is then diluted in propanediol to obtain a mixture propanediol (90%)/dry extract (10%) and the ethanol is evaporated off.

After analysis, it was determined that comparative extract EtOH comprised 0.156% by weight of xanthones and 0.043% by weight of triterpenes.

Example 2: Activity of the *Swertia chirata* Extracts C1 and C2

Protocol:

Normal human epidermal keratinocytes from three different donors (27 to 34 years old) were seeded into 6-well plates and cultured in KGM-2 medium (supplied by the company Lonza) for 72 hours at 37° C., 5% $CO_2$. The cells were subsequently incubated or not incubated (control) with 0.5% or 0.25% of *Swertia chirata* extract C1 or C2 for 48 hours. Each condition was carried out in duplicate. The total RNAs were extracted using the RNeasy 96 Plate Extraction Kit (supplied by the company Qiagen) according to supplier's recommendations. The amount and the quality of the RNAs were evaluated by Multiskan G0 (supplied by ThermoFischer). The complementary DNAs were synthesized and a transcriptome was performed on an Affymetrix® GeneChip Human Transcriptome Array 2.0 chip. The bioinformatics analysis of the genes, the expression of which is modulated by at least a factor of 2, was carried out with the Ingenuity Pathway Analysis software (IPA®, Qiagen). This software collects information on the molecule-to-molecule interactions, the biological networks and the canonical pathways in the Ingenuity Knowledge database.

Results:

▶ The *Swertia chirata* extracts C1 and C2 exhibit distinct gene regulation profiles on epidermal keratinocytes.

Each of the two *Swertia chirata* extracts modulates gene expression (between 183 and 636 genes) in epidermal keratinocytes after 48 h of treatment. At the concentration of 0.25%, the extracts regulate 2 to 2.5 times more genes compared with the concentration of 0.5%. The Venn diagrams reveal that few genes are regulated in common by the two extracts, with only 35 common genes at the concentration of 0.5% and 158 at the concentration of 0.25% (data not given).

Using the IPA® software, the analysis of the biological networks regulated by the two extracts reveals distinct mapping. These results suggest that the *Swertia chirata* extracts C1 and C2 act via distinct biological mechanisms. The *Swertia chirata* extract C1 acts preferentially by inhibiting biological pathways, whereas the *Swertia chirata* extract C2 preferentially activates biological pathways in keratinocytes.

▶ The *Swertia chirata* extract C1 inhibits the epidermal keratinocyte-mediated processes of inflammation and of degradation of the extracellular matrix.

The analysis of the biological pathways and of the genes modulated by the *Swertia chirata* extract C1 reveals that this extract is capable of reducing the interleukin IL-8-mediated inflammatory response (FIG. 1, asterisk) and of inhibiting the expression of the metalloproteinases responsible for the degradation of the extracellular matrix, MMP1 (FC=−146), MMP3 (FC=−22), MMP9 (FC=−4) and MMP10 (FC=−21) in epidermal keratinocytes compared to the non-treated control. These properties mean that the *Swertia chirata* extract C1 has cutaneous anti-inflammatory and anti-ageing roles.

▶ The *Swertia chirata* extract C2 stimulates the lipid metabolism of keratinocytes and promotes synthesis of the extracellular matrix elements.

Figure 2:
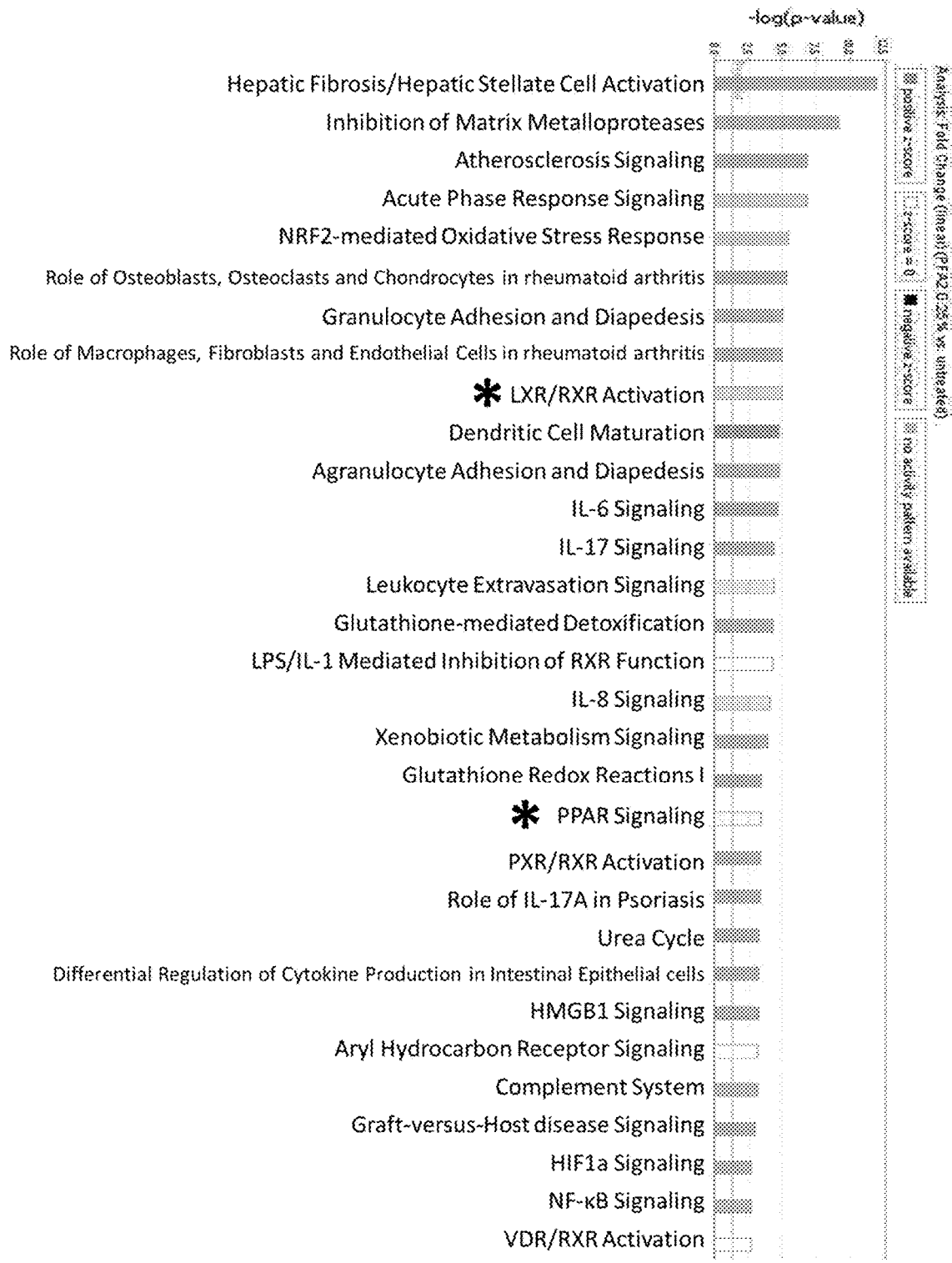
FIG. 2 is a graph representing the biological pathways modulated by the *Swertia chirata* extract C2 at 0.25% in normal human epidermal keratinocytes after 48 h of treatment.

The analysis of the biological pathways and of the genes modulated by the *Swertia chirata* extract C2 reveals that this extract is capable of stimulating biological pathways involved in the lipid metabolism of epidermal keratinocytes (LXR/RXR and PPAR pathways, FIG. 2). Likewise, the *Swertia chirata* extract 1411PFA C2 is capable of stimulating the expression of numerous genes encoding extracellular matrix elements (laminins and proteoglycans) or fibroblast-activating factors (see Table 1 below).

TABLE 1

Genes of which the expression is stimulated by the *Swertia chirata* extract C2 at 0.25% in normal human epidermal keratinocytes after 48 h of treatment

| Gene | Description | Expression level |
|---|---|---|
| DCN | decorin | 94.74 |
| FN1 | fibronectin 1 | 21.71 |
| FBN1 | fibrillin 1 | 17.29 |
| GPC3 | glypican 3 | 12.42 |
| FBLN5 | fibulin 5 | 10.75 |
| LAMA4 | laminin subunit alpha 4 | 10.46 |
| FAP | fibroblast activation protein alpha | 7.55 |
| FBLN1 | fibulin 1 | 6.93 |
| VIM | vimentin | 6.47 |
| FGF2 | fibroblast growth factor 2 | 5.63 |
| LAMA2 | laminin subunit alpha 2 | 5.52 |
| LUM | lumican | 5.30 |
| LAMC1 | laminin subunit gamma 1 | 4.30 |
| LAMB1 | laminin subunit beta 1 | 3.66 |
| LAMB4 | Laminin subunit beta 4 | 2.00 |

This extract therefore has anti-ageing properties, by virtue of its activity stimulating the synthesis of extracellular matrix components, but also skin lipid barrier-reinforcing properties for maintaining and improving the hydration of the skin.

The *Swertia chirata* Extracts According to the Invention have a Cutaneous Anti-Ageing Activity, Mediated by Complementary Activities, Either by the Inhibition of MMPs, or by the Synthesis of Matrix Elements, Respectively. Comparative Extract EtOH does not have these Specific Properties.

Example 2: Cosmetic Composition

The following compositions can be prepared conventionally by those skilled in the art. The amounts indicated below are expressed as weight percentages. The ingredients are identified in accordance with the INCI name.

A—Oil/Water Gel Emulsion

| INCI name | (% W/W) |
| --- | --- |
| Limnanthes alba (meadowfoam) seed oil | 1-10 |
| Butyrospermum parkii butter (LIPEX SHEASOFT) | 1-10 |
| Butyrospermum parkii butter extract (LIPEX SHEA TRIS) | 1-10 |
| Camellia oleifera seed oil | 1-10 |
| Caprylic/capric triglyceride | 1-10 |
| Squalane | 1-10 |
| Ammonium acryloyldimethyl-taurate/VP copolymer | 0.1-5 |
| Acrylates/C10-30 alkyl acrylate crosspolymer | 0.1-2 |
| Xanthan gum | 0.01-5 |
| Tremella fuciformis (mushroom) extract | 0.01-5 |
| Oryza sativa (rice) powder | 0.1-5 |
| Sodium hyaluronate | 0.01-3 |
| Glycerin | 1-30 |
| Polyquaternium-51 | 1-10 |
| Tocopheryl acetate | 0.1-5 |
| Niacinamide | 0.1-5 |
| Sphingomonas ferment extract | 0.01-5 |
| Polianthes tuberosa | 0.01-5 |
| Betaine | 0.1-10 |
| Sodium PCA | 0.5-5 |
| Saccharide isomerate | 0.5-5 |
| *Swertia chirata* extract C1 according to the invention | 0.001-10 |
| *Swertia chirata* extract C2 according to the invention | 0.001-10 |
| Yeast extract | 0.1-5 |
| Glycols (Caprylyl Glycol and/or Pentylene Glycol and/or Butylene Glycol and/or Propanediol) | 0.1-10 |
| Water | Qs 100 |

B—Oil/Water Cream Emulsion

| INCI name | (% w/w) |
| --- | --- |
| Jojoba esters | 1-5 |
| Limnanthes alba (meadowfoam) seed oil | 0.1-5 |
| Canola oil | 1-10 |
| Argania spinosa kernel oil | 0.1-10 |
| Moringa oil/hydrogenated moringa oil esters | 1-10 |
| C8-12 acid triglyceride | 1-5 |
| Lauroyl lysine | 1-5 |
| Camellia oleifera seed oil | 1-10 |
| Phytosteryl/octyldodecyl lauroyl glutamate | 1-5 |
| Squalane | 1-10 |
| Ammonium acryloyldimethyltaurate/VP copolymer | 1-5 |
| Cetearyl alcohol & cetearyl glucoside | 1-7 |

-continued

| INCI name | (% w/w) |
| --- | --- |
| Hydrogenated lecithin | 0.1-5 |
| Chondrus crispus (carrageenan) | 0.1-5 |
| Sclerotium gum | 0.01-2 |
| Centella asiatica leaf extract | 0.1-5 |
| Adenosine | 0.1-0.5 |
| Niacinamide | 0.1-5 |
| Secale cereale (rye) seed extract | 0.1-5 |
| Palmitoyl tripeptide-1 & palmitoyl tetrapeptide-7 | 1-5 |
| Plankton extract | 0.1-5 |
| Yeast extract | 1-3 |
| *Swertia chirata* extract C1 according to the invention | 0.001-10 |
| *Swertia chirata* extract C2 according to the invention | 0.001-10 |
| Glycyrrhiza glabra extract | 0.001-5 |
| Tranexamic cetyl ester | 0.001-5 |
| Ascorbyl glucoside | 0.001-5 |
| Water | Qs 100 |

C—Lotion

| INCI name | (% w/w) |
| --- | --- |
| Glycerin | 1-15 |
| Propanediol | 1-5 |
| Butylene glycol | 1-5 |
| Pentylene glycol | 0.1-5 |
| Caprylyl glycol | 0.01-2 |
| Polyquaternium-51 | 0.1-2 |
| Polianthes tuberosa polysaccharide | 0.1-2 |
| Sodium hyaluronate | 0.01-0.5 |
| *Swertia chirata* extract C2 according to the invention | 0.001-10 |
| Water | Qs 100 |

D—Oil

| INCI name | (% w/w) |
| --- | --- |
| Coco-caprylate/caprate | 5-15 |
| Squalane | 1-15 |
| Camellia oleifera seed oil | 1-20 |
| Helianthus annuus (sunflower) seed oil | 1-20 |
| Simmondsia chinensis (jojoba) seed oil | 1-15 |
| Caprylic/capric triglyceride | 1-15 |
| Limnanthes alba (meadowfoam) seed oil | 1-15 |
| Tocopherol | 0.1-1 |
| *Swertia chirata* extract C1 according to the invention | 0.001-10 |

These compositions can be applied to the skin every day, in the morning and/or in the evening.

The invention claimed is:

1. A *Swertia chirata* extract, wherein said extract is obtained by a method comprising a step of extracting, with supercritical $CO_2$, an alcoholic extract of *Swertia chirata*, at a temperature between 40 and 80° C. and at a pressure of between 20 and 60 MPa.

2. A cosmetic composition comprising, in a physiologically acceptable medium, the *Swertia chirata* extract according to claim 1.

3. A *Swertia chirata* extract comprising 0.035% or less by weight swertiamarin, wherein said extract is obtained by a method comprising a step of extracting, with supercritical $CO_2$, an alcoholic extract of *Swertia chirata*, at a temperature between 40 and 80° C. and at a pressure of between 20 and 60 MPa.

4. A cosmetic method for reducing an appearance of skin ageing in a subject, comprising administering an effective amount of a *Swertia chirata* extract according to claim 1 to a subject in need thereof.

5. A cosmetic method for hydrating skin of a subject and/or improving a barrier function of the skin of the subject, comprising administering an effective amount of the *Swertia chirata* extract according to claim 1 to a subject in need thereof.

6. A method for preparing a *Swertia chirata* extract, comprising a step of extracting, with supercritical $CO_2$, an alcoholic extract of *Swertia chirata*, at a temperature of between 40 and 80° C. and at a pressure of between 20 and 60 MPa.

7. The method according to claim 6, wherein, the step of extracting with supercritical $CO_2$ is carried out in the presence of an alcoholic solvent.

8. The method according to claim 7, wherein the alcoholic solvent is introduced in a content of between 1 and 10% relative to a total weight of a mixture comprising the supercritical $CO_2$ and the alcoholic solvent.

9. The method according to claim 6, wherein a polysaccharide is added to the alcoholic extract before the step of extracting with supercritical $CO_2$.

10. The method according to claim 6, wherein the method comprises the following steps:
    a) extracting *Swertia chirata* with at least one alcoholic solvent to obtain a mixture of *Swertia chirata* and the at least one alcoholic solvent;
    b) filtering the mixture obtained in a) in order to remove the plant residues and obtain a filtrate mixture;
    b') optionally, decolourizing the filtrate mixture obtained at the end of step b);
    c) adding a polysaccharide to the filtrate mixture in order to obtain a polysaccharide/extract mixture in the at least one alcoholic solvent;
    d) removing the at least one alcoholic solvent from the polysaccharide/extract mixture to obtain a dry extract/polysaccharide mixture;
    e) milling the dry extract/polysaccharide mixture obtained at the end of step d) in order to obtain a powder; and
    f) extracting with supercritical $CO_2$ the powder obtained at the end of step e), using a solvent comprising supercritical $CO_2$, at a temperature between 40 and 80° C. and at a pressure of between 20 and 60 MPa, to obtain the *Swertia chirata* extract contained in the solvent used for extracting with supercritical $CO_2$.

11. The method according to claim 10, wherein the method further comprises the following steps:
    g) filtering the *Swertia chirata* extract contained in the solvent used for extracting with supercritical $CO_2$ to obtain a filtrate comprising the *Swertia chirata* extract;
    h) diluting the filtrate comprising the *Swertia chirata* extract obtained at the end of step g) in an oil to obtain a diluted *Swertia chirata* extract in oil;
    i) filtering the diluted *Swertia chirata* extract in oil obtained at the end of step h) to obtain an oily *Swertia chirata* extract.

12. The method according to claim 10, wherein the method further comprises the following steps:
    g1) dissolving a residual powder obtained from the *Swertia chirata* extract contained in the solvent used for extracting with supercritical $CO_2$ obtained at the end of step f) in an alcoholic solvent to obtain a mixture of the residual powder and alcoholic solvent;
    h1) filtering the mixture of the residual powder and alcoholic solvent obtained at the end of step g1) to obtain a residual powder extract;
    i1) diluting the residual powder extract obtained at the end of step h1) in a glycol to obtain a diluted residual powder extract in the glycol; and
    j1) filtering the diluted residual powder extract in the glycol obtained at the end of step i1) to obtain an aqueous-alcoholic *Swertia chirata* extract.

13. The method according to claim 7, wherein the alcoholic solvent is ethanol.

14. The method according to claim 9, wherein the polysaccharide is cellulose.

15. The method according to claim 10, wherein in step 1) extracting with supercritical $CO_2$ the powder obtained at the end of step e) using the solvent comprising supercritical $CO_2$ is at a temperature between 50 and 70° C. and at a pressure between 25 and 35.

16. The method according to claim 6, wherein the method comprises the following steps:
    a) extracting *Swertia chirata* in a powder form, with ethanol, and obtaining a mixture of *Swertia chirata* and the ethanol;
    b) filtering the mixture obtained in a) in order to remove the plant residues and obtaining a filtrate mixture;
    b') optionally, decolourizing the filtrate mixture obtained at the end of step b);
    c) adding cellulose to the filtrate mixture in order to obtain a cellulose/extract mixture in ethanol;
    d) removing by evaporation the ethanol from the cellulose/extract mixture to obtain a dry extract/cellulose mixture;
    e) milling the dry extract/cellulose mixture obtained at the end of step d) in order to obtain a powder; and
    f) extracting with supercritical $CO_2$ the powder obtained at the end of step e), using a solvent comprising supercritical $CO_2$ and an alcoholic solvent, at a temperature between 40 and 80° C. and at a pressure of between 20 and 60 MPa to obtain the *Swertia chirata* extract contained in the solvent used for extracting with supercritical $CO_2$.

17. The method according to claim 16, wherein the method further comprises the following steps:
    g) filtering the *Swertia chirata* extract contained in the solvent used for extracting with supercritical $CO_2$ to obtain a *Swertia chirata* extract filtrate;
    h) diluting the filtered *Swertia chirata* extract obtained at the end of step g) in 2-ethylhexyl palmitate to obtain a diluted *Swertia chirata* extract in 2-ethylhexyl palmitate;
    i) filtering the diluted *Swertia chirata* extract obtained at the end of step h) to obtain an oily *Swertia chirata* extract.

18. The method according to claim 17, wherein the *Swertia chirata* extract filtrate obtained in step g) comprises residual alcoholic solvent from the solvent used for extracting with supercritical $CO_2$, and method further comprises a step of removing the residual alcoholic solvent by evaporation before or after diluting the filtered *Swertia chirata* extract obtained at the end of step g) in 2-ethylhexyl palmitate in step h).

19. The method according to claim 16, wherein the method further comprises the following steps:
    g1) dissolving a residual powder obtained from the *Swertia chirata* extract contained in the solvent used for extracting with supercritical $CO_2$ obtained at the end of step f) in an alcoholic solvent to obtain a mixture of the residual powder dissolved in the alcoholic solvent, wherein the alcoholic solvent being a same alcoholic solvent as the alcoholic solvent in the solvent used for extracting with supercritical $CO_2$ or another alcoholic solvent;

h1) filtering the residual powder dissolved in the alcoholic solvent at the end of step g1) to obtain a residual powder extract;

i1) diluting the residual powder extract obtained at the end of step h1) in propanediol to obtain a diluted residual powder extract in the propanediol; and j1) filtering the diluted residual powder extract in the propanediol obtained at the end of step i1) to obtain an aqueous-alcoholic *Swertia chirata* extract.

20. The method according to claim 18, wherein the mixture of the residual powder dissolved in the alcoholic solvent obtained in step g1) comprises residual alcoholic solvent from the solvent used for extracting with supercritical $CO_2$ and the alcoholic solvent used for dissolving in step g1), and the method further comprises a step of removing the residual alcoholic solvent by evaporation either before or after diluting the residual powder extract obtained at the end of step h1) in propanediol in step i1).

\* \* \* \* \*